United States Patent

Jutila et al.

[11] Patent Number: 6,156,293
[45] Date of Patent: Dec. 5, 2000

[54] MOISTENING PREPARATION

[75] Inventors: Kirsti Jutila, Espoo; Jorma Tenovuo, Turku; Eva Söderling, Rusko, all of Finland

[73] Assignee: Finnfedds Finland Ltd., Espoo, Finland

[21] Appl. No.: 09/341,106

[22] PCT Filed: Jan. 2, 1998

[86] PCT No.: PCT/FI98/00008

§ 371 Date: Aug. 26, 1999

§ 102(e) Date: Aug. 26, 1999

[87] PCT Pub. No.: WO98/29090

PCT Pub. Date: Jul. 9, 1998

[30] Foreign Application Priority Data

Jan. 3, 1997 [FI] Finland .................................... 970038

[51] Int. Cl.[7] ....................................................... A61L 9/05
[52] U.S. Cl. ............................ 424/45; 424/422; 424/428; 424/430; 424/433; 424/434; 424/435; 424/436; 424/437; 514/944; 514/969
[58] Field of Search ................................. 424/43, 49, 54, 424/422, 428, 430, 433, 434, 436, 435, 437; 514/579, 740, 556, 969, 944

[56] References Cited

U.S. PATENT DOCUMENTS 5,401,723  3/1995  Gaffar et al. ............................... 514/21
5,888,480  3/1999  Homola et al. ............................ 424/54

FOREIGN PATENT DOCUMENTS

| 6-293619 | 10/1994 | Japan . |
| 6-293625 | 10/1994 | Japan . |
| 7-309741 | 11/1995 | Japan . |
| 8-20520 | 1/1996 | Japan . |
| 8-81348 | 3/1996 | Japan . |
| 8-92060 | 4/1996 | Japan . |
| WO 91/18588 | 12/1991 | WIPO ............................... A61K 7/48 |
| WO 9118588 A1 | 12/1991 | WIPO . |
| WO91/18588 | 12/1991 | WIPO . |

*Primary Examiner*—Thurman K. Page
*Assistant Examiner*—P. M. Queeney
*Attorney, Agent, or Firm*—Nixon & Vanderhye

[57] ABSTRACT

The present invention relates to preparations alleviating the symptoms caused by drying of the mucous membranes of the body. The preparations contain trimethylglycine as an active agent. The invention also relates to the use of trimethylglycine as an agent alleviating the symptoms of dry mucous membranes in different preparations intended for the body care and hygiene, and to a method of alleviating the symptoms, caused by drying, appearing on the mucous membranes of the body.

12 Claims, No Drawings

MOISTENING PREPARATION

FIELD OF INVENTION

The present invention relates to preparations alleviating the symptoms caused by drying of the mucous membranes of the body. The preparations comprise trimethylglycine as an agent affecting the symptoms of dry mucous membranes. The invention also relates to a use of trimethylglycine as an agent alleviating the symptoms of dry mucous membranes in different preparations intended for the body care and hygiene, and to a method of alleviating the symptoms, caused by drying, appearing on the mucous membranes.

BACKGROUND OF INVENTION

The drying of mucous membranes is a common trouble in adult population, and the usual "cause" of drying is ageing. Every fourth or fifth adult suffers, for example, from dry mouth (Tenovuo, J. and Söderling, E., *Suomen Hammaslääkärilehti* 17 (1994) 972–979). A dry sensation in the mouth is more common in women than in men, which is largely due to hormonal changes: a postmenopausal drop in the oestrogen hormone concentration causes the mucous membranes of not only the vagina and female genitals but also of the mouth and eyes to dry.

The mucous membranes may also dry as a result of some external cause or situation: dry, windy weather; dry indoor air particularly in winter; a too high or too low room temperature; incorrect working position at a terminal; or watching of a TV set positioned too high may dry nasal and oral mucous membranes. Nervousness caused, for example, by a public performance; continuous speaking, for example, at a lecture; and a state of stress in which adrenalin production rises also dry the mouth.

In addition, symptoms caused by the drying of mucous membranes are also associated with many diseases and drugs used in their treatment. Dry mouth is particularly common in connection with the use of psychopharmaceuticals, and drugs used for the treatment of cardiac diseases, asthma and high blood pressure. In some rheumatic conditions and in connection with radiotherapy on the neck and nape, both mouth and eyes may dry. Further, for example, anti-allergy and anti-histamine medication dry nasal mucous membranes, particularly if nasal sprays are used frequently.

The drying of mucous membranes appears as a tight sensation, smarting, itching, pain, irritation, an uncomfortable sensation, problems in speaking, swallowing or chewing, a need to drink or to blink or moisten the eyes, to wash, etc. In addition, wounds, or apthae, appear easily on dry mucous membranes, whereby the mucous membranes easily bleed and become inflamed. A reduced amount or complete lack of saliva particularly in a dry mouth increases dental caries and, irrespective of the cause of dry mouth, oral hygiene is of primary importance if the oral mucous membranes are dry.

There are different commercially available products to alleviate the symptoms of dry mucous membranes: xylitol chewing gums and lozenges alleviating the symptoms of dry mouth and stimulating salivation; artificial saliva preparations moistening mucous membranes; eye drops and gels and nasal sprays and mist sprays alleviating the symptoms of dry eyes and nose, respectively; hormonal creams and vaginal suppositories, preparations containing lactic acid bacteria, moistening vaginal suppositories, and other such products used for alleviating the symptoms caused by drying of the vaginal mucous membranes. However, still new products are needed to alleviate and eliminate, preferably for a longer period of time and possibly on a prophylactic basis, the symptoms of dry mucous membranes, simultaneously avoiding the side effects of the currently available products.

An object of the present invention is to provide preparations that alleviate the symptoms caused by the drying of the mucous membranes of the body. Another object of the present invention is to provide a method of alleviating the symptoms, caused by drying, appearing on the mucous membranes of the mouth, eyes, nose or genitals.

BRIEF DESCRIPTION OF INVENTION

Surprisingly, it has been found that the symptoms caused by drying of mucous membranes can be alleviated by a preparation that contains trimethylglycine. Trimethylglycine can thus be contained in different preparations intended for preventing and alleviating the symptoms, caused by drying, appearing on the mucous membranes of the body.

The present invention relates to a use of trimethylglycine as an agent alleviating the symptoms and removing any unpleasant sensations caused by dry mucous membranes in preparations intended for the body care and hygiene. The present invention also relates to preparations that contain trimethylglycine as an ingredient alleviating the symptoms caused by dry mucous membranes. The present invention also relates to a method of alleviating the symptoms, caused by drying, appearing on the mucous membranes of the body by introducing a trimethylgiycine-containing preparation onto the mucous membranes.

DETAILED DESCRIPTION OF INVENTION

In the present invention, the mucous membranes of the body mean the mucous membranes of the natural apertures of the body, such as those of the mouth, eyes, nose and female genitals. The symptoms of dry mucous membranes, in turn, mean irritation, smarting, itching, a tight sensation, an unpleasant sensation, pain and other such sensations on the mucous membranes. With dry mouth are also associated, for example, problems in speaking, chewing and swallowing, aching of the tongue or salivary glands, and dental caries.

A trimethylglycine-containing preparation of the present invention can here be a preparation of oral hygiene, for example a tooth paste, powder, gel, mouthwash or mouth spray, a denture adhesive, an artificial saliva, a chewing gum, a lozenge or the like. A trimethylglycine-containing preparation according to the present invention can also be a preparation applied to the eye, such as an eye drop, eyewash, ointment or gel; or a preparation administered to the nose, such as a nasal spray, mist spray or drop. In addition, a trimethylglycine-containing preparation according to the present invention can be a preparation administered to the mucous membranes of the genitals, such as a vaginal suppository, tablet, capsule or cream, or a cream or moist tissue for intimate hygiene, or some other such preparation.

The preferred preparations of the invention include preparations used for normal every-day oral hygiene, for example tooth pastes, mouthwashes, gels and oral sprays. These preparations are particularly advantageous because they allow alleviation of dry mouth condition of varying degrees depending on the situation and the severity of the symptoms. When the dry mouth condition is not severe, it may suffice to brush the teeth twice daily with a tooth paste that contains trimethylglycine. When the symptoms are more severe, for example if salivation has greatly reduced or stopped altogether, or if temporary alleviation of the dry mouth symptoms is necessary, an oral spray containing trimethylglycine may be a suitable preparation.

The preferred preparations of the invention also include preparations administered to the eye, such as eye drops and gels. Trimethylglycine is particularly suitable for these, since it does not irritate the eye.

The preferred preparations of the invention also include preparations for moistening the mucous membranes of the genitals, whereby the symptoms of dry mucous membranes can be alleviated without a use of hormones, which some women wish to avoid.

In the present invention, trimethylglycine means a naturally occurring quaternary ammonium compound of the formula

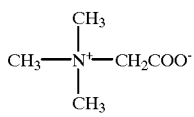

which is also generally called betaine, trimethylammonioacetate, 1-carboxy-N,N,N-trimethylmethaneaminium, inner salt, and glycinebetaine, as an anhydride or monohydrate. In the pure form, it is a white crystalline compound that is readily soluble in water but also in lower alcohols, such as methanol and ethanol. Trimethylglycine tastes sweet, and it is not toxic, so it is well suited, for example, to a tooth paste or mouthwash. Trimethylglycine does not have any irritating or allergenic effects, which is particularly important in preparations that are administered to the eye. On the contrary, trimethylglycine has been found to reduce the irritating effects of some other agents (see EP 531,387).

Trimethylglycine has a bipolar structure, and it contains several metabolically reactive methyl groups, which it can donate in enzyme-catalyzed reactions. Most organisms can synthesize trimethylglycine in small quantities, for example, for the methyl donor function, but are not able to produce nor store it in large quantities.

At cell level, trimethylglycine has been observed to protect plants particularly under stress conditions. In plants trimethylglycine functions as an osmolyte and thereby protects cells from the effects of osmotic stress. It has been used as an agent improving the preservation characteristics of plants, and as an agent improving the drought and chill resistance of growing plants. To enhance growth, trimethylglycine has also been added to fertilizers. Further, trimethylglycine has been used as an additive in animal feed and odder. It has also been observed to have pharmacological activity, e.g. it prevents detrimental effects of coccidiosis in broilers.

The best known organisms producing large quantities of trimethylglycine are plants of the genus Chenopodiaceae, such as sugar beet, and some microbes and marine invertebrates. It can be obtained e.g. from sugar beet by chromatographic methods. Trimethyiglycine is commercially available both as an anhydride and as a monohydrate from Cultor Oy, Finnsugar Bioproducts.

Synthetic long-chain alkyl ester, sulpho, and aluminium salt derivatives of trimethylglycine, commonly—and somewhat misleadingly—called 'betaine derivatives' or 'betaines' particularly in cosmetic industry, have long been used as amphoteric surfactants, for example, in tooth pastes. As examples are mentioned U.S. Pat. NoS. 4,490,355 and 4,654,161, and published European Patent Application 692, 246, which discloses an oral composition containing, for example, "a quantity of betaine that effectively reduces surface tension," which is defined as alkylbetaine. In the examples of the publication, cocoamidopropylbetaine is used. Trimethylglycine is not useful for the above-mentioned purposes, since its surfactant properties are completely different and it does not foam.

U.S. Pat. No. 5,156,845 teaches a lozenge that contains trimethylglycine hydrochloride and is intended to stimulate salivation and thereby alleviate the dry mouth symptoms. The publication teaches that trimethylglycine hydrochloride is used in the lozenge as an acedulant. Since trimethylglycine hydrochloride is strongly acidic, it differs in its properties from the trimethylglycine anhydride and trimethylglycine monohydrate with a neutral pH that are used in the present invention. If a strongly acidic compound were contained in a preparation to be applied to the mucous membranes, buffering, neutralizing agents should be added to inhibit irritation.

Trimethylglycine is known to moisten the skin. However, the surprising property of trimethylglycine presented by the present invention, i.e. the property of alleviating the symptoms of dry mucous membranes, has not been described earlier. Skin and mucous membrane differ from each other in respect of anatomy: mucous membrane is thinner and contains plenty of blood vessels, and any agents brought to the mucous membrane are more easily absorbed, whereas the function of skin is to protect the body from foreign agents, i.e. to prevent them from entering the blood circulation.

The preparation of the present invention alleviating the symptoms of dry mucous membranes contains 0.1 to 25% by weight, preferably 1 to 10% by weight, particularly 2 to 6% by weight of trimethylglycine as an anhydride or a monohydrate, based on the preparation, in water, a saline solution, an isotonic buffer solution, a water/ethanol mixture, a paste or cream base or a powdery carrier or some other such suitable base. A suitable type of preparation is selected according to the purpose. The preparation also contains ingredients and additives commonly used in the preparation concerned.

When the preparation according to the invention is a preparation of oral hygiene, such as a tooth paste or mouthwash, it can contain, in addition to trimethylglycine, remineralization-enhancing compounds, such as fluorine, calcium and phosphate compounds; abrasive agents, such as calcium carbonate, silica, calcium hydrogen phosphate or magnesium hydrogen phosphate; sweeteners, such as xylitol, sorbitol or saccharine; antimicrobial agents, such as chlorhexidine, lysozyme, lactoperoxidase, lactoferrine or antibodies; surfactants, such as sodium lauryl sulphate, sodium N-lauroyl sarcosinate, sodiumdodecylbenzenesulphate, alkylamidobetaine or monoglyceride sulphate; anti-oxidants; moistening agents, such as glycerine, sorbitol or propylene glycol; emulsifiers, such as polyvinyl alcohol; binding agents/viscosity enhancing agents, such as polyethylene glycol; gelling agents, such as carboxymethyl cellulose, hydroxyethyl cellulose or raw gum, such as gum tragacanth; stabilizers; preservatives, such as thiomersal or parabenes; flavouring agents, such as peppermint oil, menthol, anise or eucalyptus; colouring agents, such as titanium dioxide; bleaching agents, such as peroxides; and the like; and alcohol and/or water.

When the preparation according to the invention is one that is to be administered to the eye or nose, it can contain, in addition to trimethylglycine, emulsifiers, such as Pluronic F 28; moistening agents, such as glycerol; viscosity enhancing agents, such as polyethylene glycol, sodium chloride, and other such agents; and a pharmaceutical, such as an antibiotic; or essential oils (nasal preparation) and water.

When the preparation according to the invention is one that is to be administered to the vagina, for example a tablet, it can contain, in addition to trimethylglycine, for example excipients, such as methylhydroxypropyl cellulose and lactose.

The preparations according to the invention are formulated using conventional methods well known to those skilled in the art. Trimethylglycine is well suited for use with other agents, so its inclusion in a preparation will not cause any problems during the manufacture.

The use of trimethylglycine as defined in the invention in preparations intended for the body care and hygiene produces in the products an effect that alleviates the symptoms of dry mucous membranes. Since trimethylglycine also alleviates the irritating effects of the agents optionally contained in the preparation, for example the irritating effects of sodium lauryl sulphate used as a foaming agent in tooth pastes, as described in EP 531,387, trimethylglycine-containing preparations can be considered particularly friendly to mucous membranes. Trimethylglycine itself has not been found to have any antimicrobial effect on microorganisms present on mucous membranes, and it has no effect on healthy mucous membranes. Naturally occurring trimethylglycine is also a welcome alternative to synthetic ingredients used in many preparations.

The preparation according to the invention has been observed to have a long-lasting moistening effect on mucous membranes. It is possible that trimethylglycine, as a bipolar compound, adheres to the surface of the mucous membranes and remains there for a while, binding water and thereby maintaining a moist sensation.

In the following the invention will be described in greater detail by means of examples. The examples are provided only by way of illustration, and they are not to be understood as limiting the scope of the invention in any way.

EXAMPLE 1

Effect of trimethylglycine on dry mouth

A trimethylglycine tooth paste (HT1) and a reference tooth paste (HT2) were prepared. Their compositions are presented in Table 1.

TABLE 1

Composition of the tooth pastes

|  | HT1 (%) | HT2 (%) |
| --- | --- | --- |
| Trimethylglycine | 4.0 | 0 |
| Sorbitol (70%) | 50.0 | 51.05 |
| CMC 7MF | 1.0 | 1.0 |
| NaF | 0.24 | 0.24 |
| Sodiumbenzoate | 0.1 | 0.1 |
| Titanium oxide | 0.5 | 0.5 |
| Saccharin | 0.3 | 0.3 |
| Trisodiumphosphate | 1.1 | 1.1 |
| Carbobol 980 NF | 0.2 | 0.2 |
| Colour 432 | 1.0 | 1.0 |
| Silica Zeodent 113 | 20.00 | 20.00 |
| Sodium lauryl sulphate | 2.0 | 2.0 |
| Water | 19.56 | 22.51 |
| Total | 100.00 | 100.00 |

To assess the effects of trimethylglycine on dry mouth, a cross-over double blind test was carried out on ten study subjects who suffered from subjective dry mouth sensations and some of whom had been diagnosed as having the Sjogren syndrome. An analysis of the saliva showed that the ten study subjects had very low salivation ($\leq 0.6$ mlmin, xerostomia patients).

The test comprised two 2-week test periods. Each study subject was examined before and after each 2-week test period. In the cross-over double blind test, half the patients first used the reference tooth paste and then the trimethylglycine tooth paste; the other half did vice versa. All the study subjects thus used each tooth paste for two weeks, and a total of four check-ups were conducted.

At the first check-up the study subjects were given accurate instructions concerning the study, and any medication used was recorded. Likewise, the colour and condition of the mucous membranes of each study subject, and the appearance and condition of the tongue were recorded.

For a microbiological sample, the study subjects rinsed their mouths for one minute with 5 ml of a saline solution, of which 2×100 $\mu$l were recovered in TSB-containing tubes (Tryptic Soy Broth, Difco). The tubes were kept at $-20°$ C. before cultivation. The samples were cultured for *Streptococcus mutans* bacteria using a Bacto Mitis Salivarius Agar dish (Difco) which contained 1.8 mg/l of bacitracin (Sigma), (3 d, 37° C., 7% $CO_2$); for lactobacilli using Bacto Rogos Agar dishes (Difco; 3 d, 37° C., anaerobically); for yeasts using Bacto Sabouraud Dextrose Agar dishes (Difco; 2 d, 37° C., anaerobically); and for total anaerobes (total aa) using Blood Agar Base dishes (Difco) which contained 5% of sheep blood. The colony number of the microbes was counted.

After the test period, an inquiry was also conducted on subjective dry mouth sensations using a questionnaire, which is presented in Table 2. At the last check-up, the study subjects were requested to compare the two tooth pastes they had used.

On visual inspection of the study subjects' oral mucous membranes, no significant changes associated with the use of tooth paste were observed in either of the test groups. Further, no significant changes associated with the use of tooth paste were observed in the microbiological parameters describing the health condition of the mouth.

Instead, the study subjects' subjective sensations after the use of the trimethylglycine tooth paste and the reference tooth paste were observed to have changed in a statistically significant manner. Table 2 shows the questionnaire and the changes in the study subjects' subjective sensations. HT1 is the group that used the trimethylglycine tooth paste, HT2 is the group that used the reference tooth paste, and n is the number of study subjects.

TABLE 2

Questionnaire: How did the use of paste HT1/HT2 affect your sensations of dry mouth?

| | | Changes in xerostomia patients' subjective sensations | | | | |
|---|---|---|---|---|---|---|
| | | HT1 (n = 10) | | | HT2 (n = 10) | |
| | | no effect | increased | reduced | no effect | increased | reduced |

Question 1

How dry is your mouth or tongue in daytime?
very dry (1)-rather dry (2)-not dry (3)
- HT1: no effect 4/10, reduced 6/10
- HT2: no effect 10/10

Question 2

How dry is your mouth or tongue at night?
very dry (1)-rather dry (2)-not dry (3)
- HT1: no effect 7/10, reduced 3/10
- HT2: no effect 10/10

Question 3

Does your mouth or tongue hurt or smart a lot?
always (1)-sometimes (2)-never (3)
- HT1: no effect 9/10, reduced 1/10
- HT2: no effect 6/10, reduced 4/10

Question 4

Are your lips dry or do they smart?
always (1)-sometimes (2)-never (3)
- HT1: no effect 9/10, reduced 1/10
- HT2: no effect 8/10, reduced 2/10

Question 5

Do you have to drink often in daytime?
always (1)-sometimes (2)-never (3)
- HT1: no effect 7/10, reduced 3/10
- HT2: no effect 10/10

Question 6

Do you have to drink often at night?
always (1)-sometimes (2)-never (3)
- HT1: no effect 8/10, reduced 2/10
- HT2: no effect 10/10

Question 7

Do you drink at meals?
always (1)-sometimes (2)-never (3)
- HT1: no effect 10/10
- HT2: no effect 10/10

Question 8

Do you wake up at night because of dry mouth?
always (1)-sometimes (2)-never (3)
- HT1: no effect 8/10, reduced 2/10
- HT2: no effect 10/10

Question 9

Swallowing is very difficult (1)-somewhat difficult (2)-easy (3)
- HT1: no effect 10/10
- HT2: no effect 10/10

Question 10

Chewing is very difficult (1)-somewhat difficult (2)-easy (3)
- HT1: no effect 10/10
- HT2: no effect 9/10, reduced 1/10

Question 11

Speaking is very difficult (1)-somewhat difficult (2)-easy (3)
- HT1: no effect 9/10, reduced 1/10
- HT2: no effect 10/10

Question 12

How many times per day did you brush your teeth during the test period? _____
duration/times Question 13

Would you like to continue using the paste?    o yes    o no    why _____

Question 14

If the paste alleviated symptoms of dry mouth, how long did the effect last?    <10 min    about ½ hour    >1 hour Question 15

Did the taste of the paste appeal to you?    o yes    o no

Question 16

Was the construction of the paste appropriate?    o yes    o no

Question 17

Suggested improvements with respect to the properties of the paste _____

Question 18

Other comments: _____

Question 19

Did you notice any difference between pastes 1 and 2? _____

TABLE 2-continued

Questionnaire: How did the use of paste HT1/HT2 affect your sensations of dry mouth?

| | Changes in xerostomia patients' subjective sensations | |
|---|---|---|
| Question 20 | HT1 (n = 10) | HT2 (n = 10) |
| Which paste (1 or 2) did you find more pleasant to use? | | |

When the study subjects used the trimethylglycine-containing tooth paste, eight questions indicated a reduction in the symptoms: question 1, 60%; question 2, 30%; question 3, 10%; question 4, 10%; question 5, 30%; question 6, 20%; question 8, 20%; and question 11, 10%. Question 1 (how the paste affected sensations of dry mouth in daytime), the reduction in the symptoms was statistically significant (p=0.0034). Two other questions (questions 2 and 5) also yielded indicative results (p<0.1).

When the study subjects in the reference group used the reference tooth paste, two questions indicated an increase in the symptoms. On answering the question "Does your mouth or tongue hurt or smart a lot?" (question 3), 4 study subjects out of 10 (40%) felt that they had more symptoms; and on answering the question "Are your lips dry or do they smart?" (question 4), 2 study subjects out of 10 (20%) felt that the symptoms had increased. One question (question 10) indicated a reduction in the symptoms: 1 out of 10 (10%) felt that chewing had become easier. The results are not, however, statistically significant.

When the study subjects were asked which tooth paste they would prefer, 8 (80%) considered the trimethylglycine-containing paste more pleasant. They pointed out a variety of reasons: a foaming property (50%, n=5), a moistening effect (30%, n=3), the dry tongue felt better (10%, n=1), the gums felt fresher and moister (20%, n=2), and a good taste (20%, n=2). Two study subjects considered the reference paste to be more pleasant: one of them (10%, n=1) felt that the reference tooth paste tasted milder as compared with the trimethylglycine tooth paste, and the other (10%, n=1) considered the reference tooth paste to foam less and cause less smarting.

EXAMPLE 2

Effect of trimethylglycine on healthy oral mucous membranes

To assess the effect of trimethylglycine on healthy oral mucous membranes, 17 voluntary students of dentistry were divided into two groups: one group (n=8) used the tooth paste (HT1) of Example 1 containing 4% trimethylglycine, and the other group (n=9) used the reference tooth paste (HT2) of Example 1. The test was conducted as a double blind test. Before the test, all the study subjects used the same commercially available tooth paste (Pepsodent Super Fluor®) so that their starting condition was as identical as possible. Also, the study subjects were given accurate instructions as to the use of the tooth paste.

The study subjects' oral mucous membranes were checked both before the use of the test tooth paste and after a 2-week use. At the check-up, all plaque was recovered from half the teeth (from sectors I and IV). The plaque was weighed (wet weight/mg) and transferred to a TSB-containing tube, which was kept at −20° C. The plaque was cultured for *S. mutans* and total anaerobes (total aa) in the manner described in Example 1. The colony number was counted.

The results obtained in the plaque analysis are shown in Table 3. The quantity of plaque was determined on the basis of its wet weight (mg/half the mouth) and the number of total anaerobes in the plaque. The results are given as mean values (±standard deviation) before a 2-week period of use of the product (A) and after the period (B). In Table 3, HT1 is the test group that used the trimethylglycine tooth paste, and HT2 the group that used the reference tooth paste. MS stands for mutans streptococci, and n is the number of study subjects.

TABLE 3

Quantity of dental plaque and mutans streptococci

| | Group HT1 | | Group HT2 | |
|---|---|---|---|---|
| | A | B | A | B |
| Wet weight of plaque (mg/half the mouth) | 12.8 (±14.4) | 15.1 (±13.1) | 7.1 (±2.9) | 8.1 (±3.9) |
| Total aa of plaque | 8.3 (±0.6) | 8.6 (±0.4) | 8.2 (±0.4) | 8.4 (±0.5) |
| MS of plaque | 4.2 (±2.4) | 4.7 (±1.6) | 4.9 (±2.3) | 4.9 (±2.2) |
| Number of study subjects | 8 | | 9 | |
| Statistical significance[1] | ns | | ns | |

[1]Statistical testing was conducted using a paired t-test; $p \geq 0.05$ = ns (= not significant); $p < 0.05$ = *; $p < 0.01$ = ; $p < 0.001$ = *.

From the study subjects was also recovered total saliva. Salivation was stimulated with paraffin for 30 seconds, after which 2 ml of saliva was recovered. The salivation rate (time) was recorded. For culturing purposes, 100 µl of saliva was added to a TSB tube, which was kept at -20° C. The saliva was cultured for mutans streptococci (MS) under the same culture conditions as the plaque; for lactobacilli (LB) using Rogosa Agar dishes; and for yeasts using Sabouraud Agar dishes, as described in Example 1. The colony number of the microbes was counted.

The results of the saliva microbe analysis are shown in Table 4. The results are given as mean values (±standard deviation) before a 2-week period of use of the product (A) and after the period (B). In Table 4, HT1 is the test group that used the trimethylglycine tooth paste, HT2 is the group that used the reference tooth paste, and n is the number of study subjects. LB stands for lactobacilli, and MS for mutans streptococci.

TABLE 4

| | Microbe data of saliva | | | |
| --- | --- | --- | --- | --- |
| | Group HT1 | | Group HT2 | |
| | A | B | A | B |
| LB of saliva | 3.0 | 2.8 | 2.6 | 2.4 |
| | (±2.6) | (±2.4) | (±2.0) | (±1.9) |
| MS of saliva | 4.3 | 4.7 | 4.7 | 4.7 |
| | (±2.0) | (±0.9) | (±1.9) | (±1.9) |
| Yeasts of saliva | 1.7 | 0.8 | 2.6 | 2.4 |
| | (±1.8) | (±1.5) | (±1.5) | (±1.8) |
| Number of study subjects | 8 | | 9 | |
| Statistical significance[1] | ns | | ns | |

[1]Statistical testing was conducted using a paired t-test; $p \geq 0.05$ = ns; $p < 0.05$ = *; $p < 0.01$ = ; $p < 0.001$ = *.

The tooth paste groups did not differ from each other with respect to the LB, MS and yeast concentrations of saliva in a manner that would be statistically significant, when the groups were compared before the test period started (Student's t-test). The quantity of plaque (mg/half the mouth), the total aa and MS levels did not differ at that point, either. No statistically significant changes that could have been associated with the use of the trimethylglycine tooth paste or the reference tooth paste were observed in any parameter (paired t-test).

In the light of the above results, the use of trimethylglycine in a tooth paste does not seem to prevent the growth of mutans streptococci or microbes belonging to the normal oral flora, but above all it does not enhance their growth, either. The study subjects found the taste of the trimethylglycine tooth paste pleasant, and no unpleasant sensations appeared.

What is claimed is:

1. A method of alleviating the symptoms caused by drying of the mucous membranes of the natural apertures of the body comprising topically applying onto the mucous membranes a composition containing trimethylglycine as an anhydride or monohydrate.

2. A method of alleviating the symptoms caused by drying of the mucous membranes of the natural apertures of the body comprising topically applying onto the mucous membranes of the mouth a composition containing trimethylglycine as an anhydride or monohydrate.

3. The method of claim 2 wherein the composition is applied as a tooth paste, tooth gel, mouthwash or spray.

4. A method of alleviating the symptoms caused by drying of the mucous membranes of the natural apertures of the body comprising topically applying onto the mucous membranes of the eye a composition containing trimethylglycine as an anhydride or monohydrate.

5. The method of claim 4 wherein the composition is applied as an eye drop, eye gel or ophthalmic ointment.

6. A method of alleviating the symptoms caused by drying of the mucous membranes of the natural apertures of the body comprising topically applying onto the mucous membranes of the nose a composition containing trimethylglycine as an anhydride or monohydrate.

7. The method of claim 6 wherein the composition is applied as a real nasal spray, mist spray or drop.

8. A method of alleviating the symptoms caused by drying of the mucous membranes of the natural apertures of the body comprising topically applying onto the mucous membranes of the vagina a composition containing trimethylglycine as an anhydride or monohydrate.

9. The method of claim 8 wherein the composition is applied as a vaginal cream or suppository.

10. The method of claim 1, 2, 4, 6 or 8 wherein the composition contains 0.1 to 25% by weight trimethylglycine, based on the entire composition, together with a pharmaceutically acceptable base.

11. The method of claim 10 wherein the composition contains 1 to 10% by weight trimethylglycine, based on the entire composition, together with a pharmaceutically acceptable base.

12. The method of claim 11 wherein the composition contains 2 to 6% by weight trimethylglycine, based on the entire composition, together with a pharmaceutically acceptable base.

* * * * *

UNITED STATES PATENT AND TRADEMARK OFFICE
CERTIFICATE OF CORRECTION

PATENT NO.    : 6,156,293
DATED         : December 5, 2000
INVENTOR(S)   : JUTILA et al It is certified that error appears in the above-identified patent and that said letters patent is hereby corrected as shown below:

Cover Sheet change the Assignee information to read as follows:

[73] Assignee: Finnfeeds Finland Ltd., Espoo, Finland.

Signed and Sealed this

First Day of May, 2001

Attest:

NICHOLAS P. GODICI

Attesting Officer    Acting Director of the United States Patent and Trademark Office